United States Patent
Kiss et al.

(10) Patent No.: US 7,481,931 B2
(45) Date of Patent: Jan. 27, 2009

(54) METHOD OF CLEANING AND QUALIFYING A DIALYSIS FILTER AND MACHINE FOR SAME

(75) Inventors: Denes Kiss, Bâle (CH); Jean-Marc Widmer, Lignières (CH)

(73) Assignee: Ciposa S.A., Saint-Blaise (CH)

( * ) Notice: Subject to any disclaimer, the term of this patent is extended or adjusted under 35 U.S.C. 154(b) by 455 days.

(21) Appl. No.: 10/513,569

(22) PCT Filed: May 6, 2003

(86) PCT No.: PCT/CH03/00290

§ 371 (c)(1),
(2), (4) Date: Nov. 4, 2004

(87) PCT Pub. No.: WO03/092871

PCT Pub. Date: Nov. 13, 2003

(65) Prior Publication Data

US 2005/0173343 A1    Aug. 11, 2005

(30) Foreign Application Priority Data

May 6, 2002 (FR) .................................. 02 05617

(51) Int. Cl.
*B01D 63/00* (2006.01)
*C02F 9/00* (2006.01)
*B01D 11/00* (2006.01)

(52) U.S. Cl. .............................. 210/321.71; 210/257.2; 210/645; 210/646; 604/4

(58) Field of Classification Search ................. 210/646, 210/321.71, 636, 321, 69, 650, 321.6, 321.8, 210/195.2, 257.2, 257, 645; 604/4
See application file for complete search history.

(56) References Cited

U.S. PATENT DOCUMENTS 4,267,040 A * 5/1981 Schal ......................... 210/104
4,444,597 A   4/1984 Gortz et al.

(Continued)

FOREIGN PATENT DOCUMENTS

DE       34 42 744 A1    6/1986

(Continued)

*Primary Examiner*—Ana M Fortuna
(74) *Attorney, Agent, or Firm*—Davis & Bujold, P.L.L.C.

(57) ABSTRACT

The invention relates to a method and a machine for cleaning and qualifying a dialysis filter, which can be used to monitor changes in the filter over the course of the use life thereof while guaranteeing a high degree of safety in relation to possible contamination by blood residues. The inventive machine (10) comprises three treatment stations (11) which are independent from one another and which are used to regenerate simultaneously three dialysis filters (100). Each of the stations (11) rinses a dirty filter using a cleaning liquid and each station comprises a cleaning unit consisting of two distinct liquid transfer circuits. Two drains (17a, 17b), which are connected at each end of the blood compartment of the filter (100), are used to drain the contaminated liquid and the blood residues directly into drain containers (18a, 18b). The different cycles of the machine are controlled by way of a keyboard (19), which is associated with a display screen (20), and are managed automatically by a computer. Moreover, the machine also comprises devices for checking the performances of the treated filter, way of recording and saving filter data after each qualification and way (40) of identifying the filter.

11 Claims, 4 Drawing Sheets

U.S. PATENT DOCUMENTS

| | | | |
|---|---|---|---|
| 4,517,081 A | | 5/1985 | Amiot et al. |
| 4,713,171 A | * | 12/1987 | Polaschegg ............... 210/110 |
| 4,762,620 A | * | 8/1988 | Sama .......................... 210/646 |
| 4,894,164 A | * | 1/1990 | Polaschegg ............... 210/646 |
| 4,950,395 A | * | 8/1990 | Richalley .................. 210/195.2 |
| 5,486,286 A | | 1/1996 | Peterson et al. |
| 5,702,597 A | * | 12/1997 | Chevallet et al. ......... 210/195.2 |
| 5,792,367 A | * | 8/1998 | Mattisson et al. ........... 702/100 |
| 5,814,179 A | * | 9/1998 | Ohmori et al. .............. 156/294 |
| 5,897,832 A | | 4/1999 | Porter |
| 6,132,616 A | * | 10/2000 | Twardowski et al. ........ 210/646 |
| 7,115,206 B2 | * | 10/2006 | Chevallet et al. ............ 210/791 |
| 7,125,393 B2 | * | 10/2006 | Brauer et al. ............... 604/4.01 |
| 7,186,342 B2 | * | 3/2007 | Pirazzoli et al. ............. 210/636 |

FOREIGN PATENT DOCUMENTS

| | | |
|---|---|---|
| EP | 0 065 442 | 11/1982 |
| WO | WO 02/098491 A1 * | 12/2002 |

* cited by examiner

FIG. 4 ly automatic
METHOD OF CLEANING AND QUALIFYING A DIALYSIS FILTER AND MACHINE FOR SAME This application is a national stage completion of PCT/CH03/00290 filed May 6, 2003 which claims priority from French Application Serial No. 02/05617 filed May 6, 2002.

TECHNICAL DOMAIN

The present invention concerns a method of cleaning and qualifying a dialysis filter comprising a first dialysate compartment having a first connecting tip and a second connecting tip, and a second blood compartment comprising two conduits that are coupled at each extremity of said compartment, said two compartments being separated by an ultrafiltration membrane that is liquid-permeable but not air-permeable, located inside the filter.

It also concerns a machine for cleaning and qualifying a dialysis filter comprising a first dialysate compartment having a first connecting tip and a second connecting tip, and a second blood compartment comprising two conduits that are coupled at each extremity of said compartment, the two compartments being separated by an ultrafiltration membrane that is liquid-permeable but not air-permeable, located inside the filter, for use with the method.

Patients with kidney conditions are periodically subjected to hemodialysis in order to remove toxic waste from their blood. This medical treatment requires the use of dialysis machines in which the blood is cleansed by passing through a semi-permeable membrane. This membrane is located in a filter allocated to each patient which must be regenerated in certain cases, that is, cleaned and controlled after each treatment and prepared for the next treatment. This cleaning takes place in certain countries where it is permitted by law, whereas in other countries the single use principle is imposed for safety reasons, with cleaning and reuse being unacceptable even it entails substantial economic benefit. Cleaning must be done with the utmost precaution to prevent possible virus transmission through the cleaning machine to other patients. In addition, proper records of the regenerations must be kept to eliminate the risk of mixing up filters, to ensure that the filters are in good condition, and to prevent deteriorated filters from being reused.

PRIOR ART TECHNIQUE

Continuous cleaning machines function on the principle according to which the flow of cleaning liquid, circulating through a single circuit, passes simultaneously through the dialysate compartment and the blood compartment of the dialysis filter. Despite utmost precautions, this embodiment can cause the dialysis machine to become polluted by bacteria or microbes contained in the blood compartment of a dialysis filter, polluted by another patient. Measuring the volume in the blood compartment, which is one of the measurements required by the AAMI, takes place in these machines by precisely measuring a volume collected through the filter and subtracting the volume in said compartment. The ultrafiltration rate cannot be measured this way. Furthermore, these machines do not allow for monitoring the evolution of filter parameters as a function of the number of times used or other criteria established by the doctor attending the patient to whom the filter is allocated.

U.S. Pat. No. 5,897,832 describes a method of cleaning dialysis filters whose particular feature is the use of ozonized water as the rinsing liquid by flux inversion. The sterilization period extends over about 30 minutes.

U.S. Pat. No. 4,444,597 describes a completely automatic process for cleaning and disinfecting a dialysis machine that comprises a phase of identifying the filters and then a phase of cleaning according to predetermined cycles.

European Patent Application No. 0 065 442 A1 describes a method of cleaning and unclogging a system of semipermeable hollow fibers, specifically in a dialysis filter, proceeding with a retrofiltration cleaning system to unclog the fibers. Note, however, that the hollow fiber circuit and the exterior circuit are coupled in the same global circuit using valves in such a way that an error in manipulation or a defect in the valves could cause rinse liquid to pass from the blood compartment into the dialysate compartment and contaminate the dialyzer.

EXPLANATION OF THE INVENTION

The present invention proposes remedying these various disadvantages by offering a method and a dialysis filter cleaning machine which also permits the filter to be qualified, said method guarantying complete safety insofar as the risk of machine contamination by blood residue is concerned. In addition, this method permits analysis of filter evolution during successive uses and thereby allows future problems associated with the filter to be foreseen and anticipated. Finally, because the machine and the filters treated are controlled automatically, the risk of faulty manipulation or errors is completely eliminated.

The method according to the invention, as defined in the preamble, is characterized in that, in a first cleaning step, a first rinsing circuit is defined comprising said first dialysate compartment, said first connecting tip connected to the lower portion of said first compartment, and said second connecting tip connected to the upper portion of said first compartment; in that a second rinsing circuit is defined comprising said second blood compartment and the two coupled conduits at the extremities of said compartment, in that only the first rinsing circuit is supplied with rinsing and disinfection liquid injected into said first tip of said first connecting tip connected to the lower portion of said first dialysate compartment; in that exclusively the said second rinsing circuit is supplied with cleaning and disinfecting liquid present in said first rinsing circuit by ultrafiltration through said ultrafiltration membrane that is liquid-permeable but not air-permeable; and in that during a second qualifying step, the ultrafiltration rate of said ultrafiltration membrane that is liquid-permeable but not air-permeable is determined by filling said first dialysate compartment and said second blood compartment with a liquid, by generating depressurization in said first dialysate compartment by said second connecting tip connected to the upper portion of said first dialysate compartment, so as to suction at least a quantity of liquid that is essentially equivalent to the liquid contained in said second blood compartment by ultrafiltration through said ultrafiltration membrane that is liquid-permeable but not air-permeable, and by determining the slope of the curve of the volume of liquid suctioned as a function of time.

According to a preferred embodiment, during said second qualifying step, at least one of the two conduits that are coupled at each extremity of said second blood compartment is placed in contact with the atmosphere.

During said second qualifying step, next the depressurization in said first dialysate compartment is advantageously regulated by said second connecting tip connected to the upper portion of said first dialysate compartment by means of a pressure regulator connected to said second tip.

During said second qualifying step, it is advantageous to continually collect the liquid withdrawn from said first dialysate compartment in a measurement container.

During said second qualifying step, according to a preferred method, the liquid withdrawn from said first dialysate compartment is collected in a measurement container that is appropriate for defining a logarithm measurement scale.

During said second qualifying step, the volume of liquid withdrawn from said first dialysate compartment is advantageously measured by determining the variations in height of the liquid in the measurement container using a measurement probe.

Finally, during said second qualifying step, data is preferably automatically recorded concerning the qualified filter, the parameters of the patient to whom the filter is attributed, and the results of the measurements performed.

The machine for implementing the method of the invention as defined in the preamble is characterized in that it comprises a first rinsing circuit comprising said first dialysate compartment, said first connecting tip being connected to the lower portion of said first compartment and said second connecting tip being connected to the upper portion of said first compartment; in that it comprises a second rinse circuit comprising said second blood compartment and the two conduits coupled at the extremities of said second compartment; in that it comprises means for supplying exclusively said first rinse circuit with cleaning and disinfecting liquid injected through said first tip connected to the lower portion of said first dialysate compartment; in that it comprises means for supplying exclusively said second rinse circuit with cleaning and disinfecting liquid present in said first rinse circuit by ultrafiltration through said ultrafiltration membrane that is liquid-permeable but not air-permeable; in that it comprises means of qualifying to determine the ultrafiltration rate of said ultrafiltration membrane that is liquid-permeable but not air-permeable, comprising means of generating depressurization within said first dialysate compartment by said second connecting tip connected to the upper portion of said first dialysate compartment in order to suction at least a quantity of liquid that is essentially equivalent to the quantity contained in said second blood compartment by ultrafiltration through said ultrafiltration membrane that is liquid-permeable but not air-permeable; and means for determining the slope of the curve of the volume of liquid suctioned as a function of time.

In the preferred form of embodiment of the machine, the two conduits coupled at the extremities of said second blood compartment are respectively associated with two throttle valves and in that said conduits respectively flow into recovery containers.

Advantageously, the machine comprises a pump connected to the connecting tip connected to the upper portion of said first dialysate compartment.

In the preferred form of embodiment, the machine comprises a pressure regulator also connected to the connecting tip joined to the upper portion of said first dialysate compartment.

The machine preferably comprises a measurement container into which the pump opens and a measurement probe for measuring variations in the level of liquid in said container.

The walls of the measurement container are advantageously are provided with an essentially logarithmic measurement scale in order to maintain the same degree of precision regardless of the volume of liquid collected in this container.

The means for qualifying the filter advantageously comprise automatic means for identifying the filter and the operator of the machine. Said filter identification means preferably consists of one transponder card that is respectively attributed to each filter and each operator.

According to an advantageous design, the machine comprises one card reader respectively attributed to each filter and each operator.

It preferably comprises a means for automatically recording the data from the qualified filter, the parameters of the patient to whom the filter is attributed, and the results of the measurements performed.

DESCRIPTIVE SUMMARY OF THE DRAWINGS

The present invention will be better understood with reference to the description of one example of a preferred embodiment of the machine according to the invention and the method using the machine, as well as the attached drawings, wherein.

HOW TO ACHIEVE THE INVENTION

With reference to the drawings, the cleaning and qualifying machine 10 (see FIG. 1) for a dialysis filter 100 (see FIG. 2) comprises one compartment for the dialysate (100a) and one compartment for the blood (100b) separated by a membrane 110 that is primarily liquid-permeable but not air-permeable, designed for use with the method according to the invention. On the one hand, the method provides a high level of protection from the risk of contamination and on the other hand, it offers automation, monitoring, and recording of all the measurements performed. This cleaning principle is based on the complete separation of the circuits respectively corresponding to dialysate compartment 100a and blood compartment 100b in such a way that no direct communication can exist between the liquids circulating through these two compartments other than through filtration membrane 110 itself.

During the cleaning phase of the method, said filter 100 is rinsed using a suitable rinse liquid injected into the lower portion of dialysate compartment 100a and partially recovered in the upper portion of the same compartment. The rinse liquid passing through this dialysate compartment 100a, connecting tip 13 joined to the lower portion of said compartment, and connecting tip 15 joined to the upper portion of said compartment define a first rinse circuit. A fragment of said rinse liquid penetrates into blood compartment 100b of the filter by ultrafiltration through membrane 110 of said filter. This fragment of rinse liquid, filtered by the membrane through which it passes, serves to rinse the blood compartment. The fragment of this rinse liquid drives the residual substances that have been traveling through the blood and that may have been fixed within the blood compartment, after having detached them from the walls of the blood compartment. The fragment of liquid and the residual substances constitute the mixture circulating in a second circuit defined by the second blood compartment 100b and two conduits 17a and 17b (see FIG. 2) that are connected to the extremities of this compartment and which are respectively equipped with two closure valves called throttle valves 17c and 17d. This mixture is evacuated towards recovery receptacles 18a and 18b or directly to the drains or to a waste evacuation reservoir. These residual substances that circulate in the second circuit cannot contaminate the first circuit separated from the first by the membrane of the dialysis filter.

Qualifying the filter is done by automatically and continuously measuring the ultrafiltration rate of the filter membrane by measuring the volume in the blood compartment. The object is to detect broken or plugged fibers in this filter. This data is processed, recorded, and stored automatically in the processor in order to track the performance evolution of the filters over time. The qualification operation will be described in detail with reference to FIG. 4.

Figure 1:
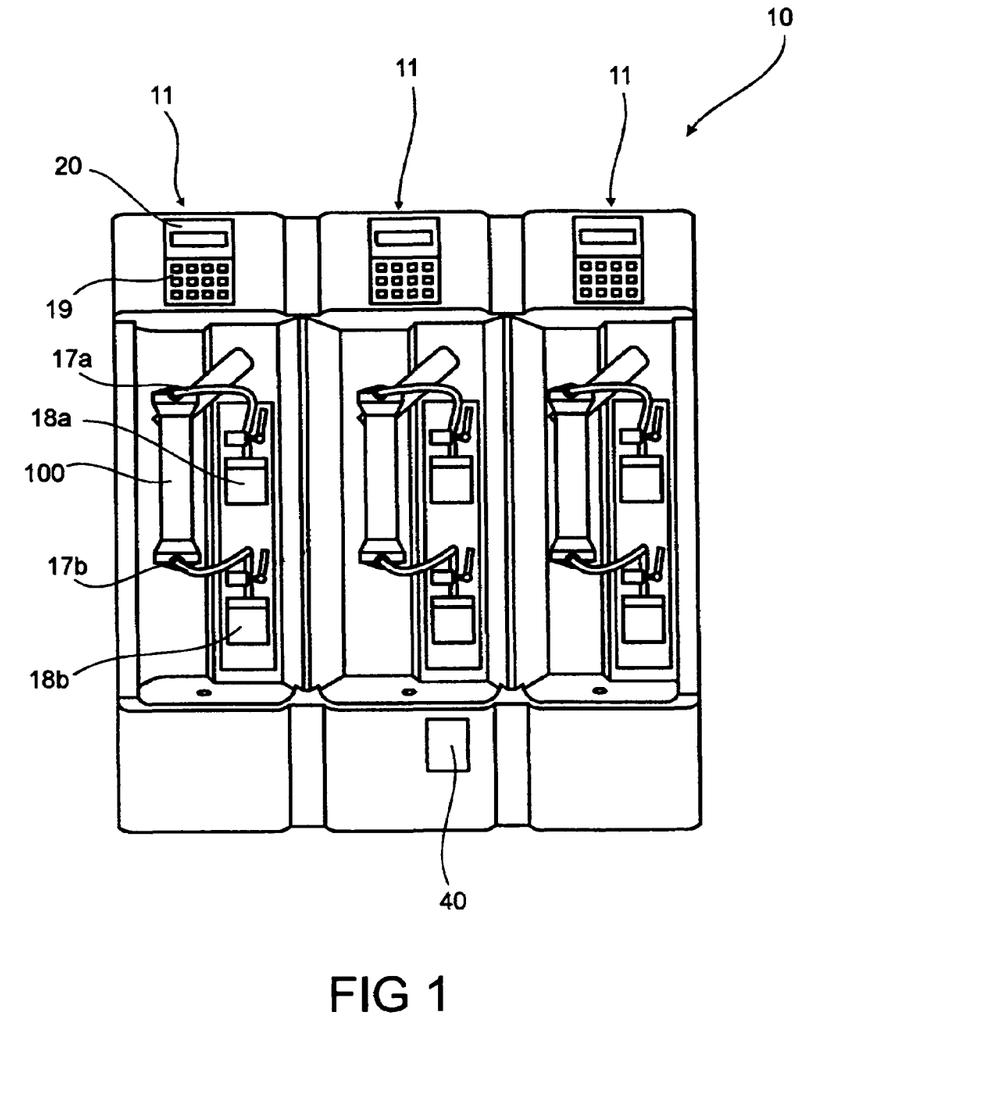
FIG. 1 is a view of the entire dialysis filter cleaning and qualifying machine according to the invention.
Figure 2:
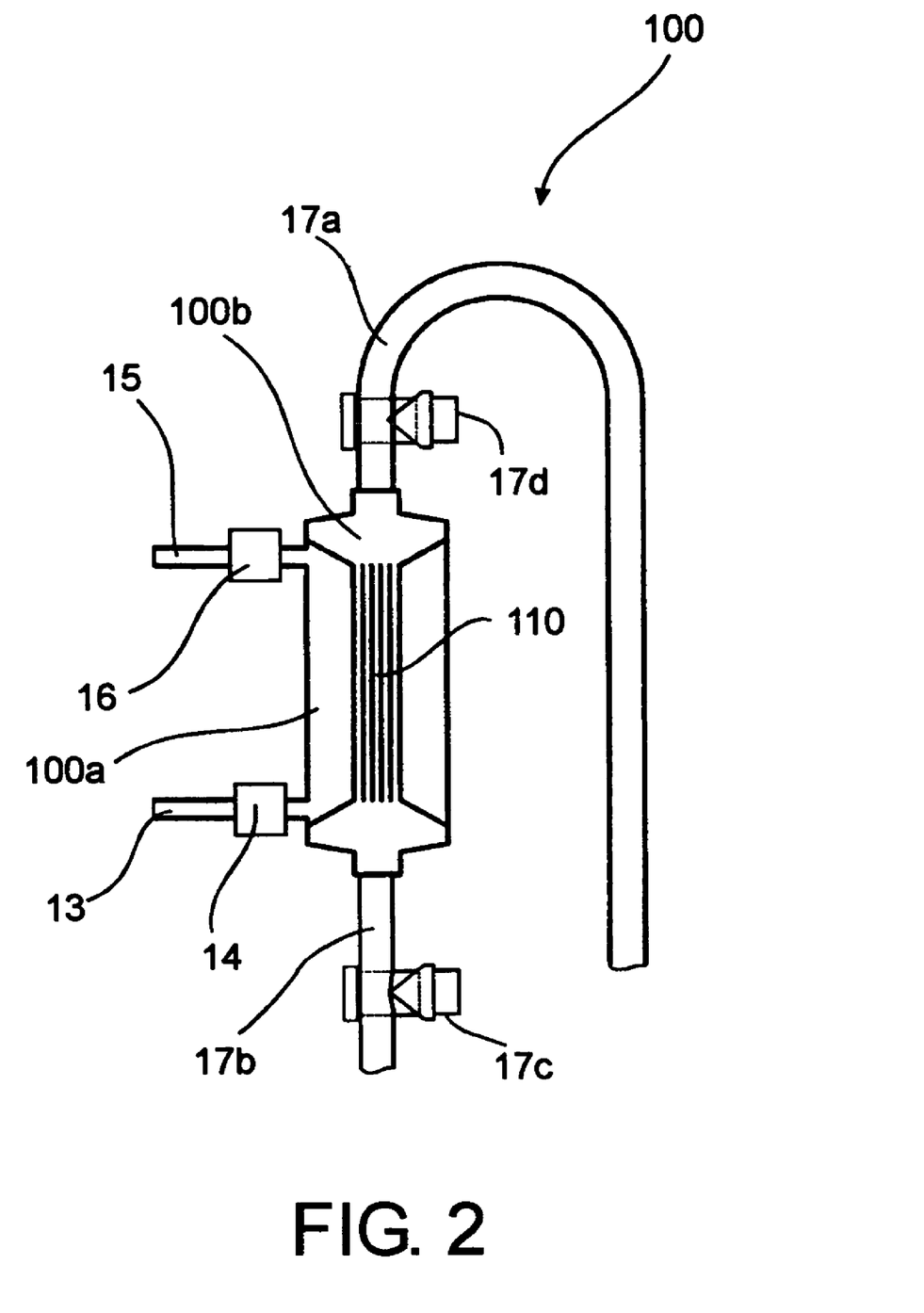
FIG. 2 is a detailed view of the filter treated by the machine of FIG. 1 with inlets and outlets for the rinse circuits.

The machine 10 for cleaning and qualifying a dialysis filter 100 as shown in FIG. 1 combines within the same structure three processing stations 11 which are totally independent from one another, thereby allowing three filters to be regenerated simultaneously. These dialysis filters 100, such as the one shown in detail in FIG. 2, have a dialysis compartment 100a designed to contain a dialysate and a blood compartment 100b through which the blood passes, said two compartments being separated by a membrane 110 that is liquid-permeable but not air-permeable. In addition, the porous walls are constructed so as to prevent virus and bacteria from passing through the pores. Each processing station 11 is designed to effect cleaning by rinsing a dirty filter after use using the appropriate cleaning liquid, as well as to disinfect the machine. A rinse liquid, preferably a disinfectant as previously described, circulates through to accomplish this. These processing stations are associated with control devices 12 for performance of the treated filter and with means for recording and storing the data from the filters after each qualifying measurement is performed.

A processing station 11 consists of a cleaning unit comprising a first rinse circuit comprising dialysate chamber 100a, connecting tip 13 connected to the lower portion of filter 100, and connecting tip 15 connected to the upper portion of filter 100, traversed by a suitable cleaning liquid injected into the lower portion of the dialysate chamber and partially recovered at the upper portion of this same compartment. This cleaning liquid flows to connecting tip 13 at the lower portion of dialysate compartment 100a of the filter associated with a blocking valve 14. The liquid is evacuated through connecting tip 15 toward a recovery container after dialysate compartment 100a has been rinsed, said tip being connected to a blocking valve 16. As mentioned above, a fragment of this liquid passes through the filter membrane and penetrates the blood compartment in order to rinse it.

The second rinse circuit consists of this fragment of cleaning liquid having traversed membrane 110. This circuit is defined by two conduits 17a and 17b that are connected to each extremity of blood compartment 100b of the filter and allow direct evacuation of the dirty liquid and residual bloody substances into one of the recovery containers 18a and 18b (see FIG. 1). This second circuit is totally independent of the first circuit corresponding to dialysate compartment 100a. This guarantees that no viruses, germs, or pathogens originating from each patient and contained in said blood compartment in the filter can pollute the dialysis machine, since membrane filter 110 does not allow them to pass through.

As shown in FIG. 1 the various cycles of the cleaning machine are controlled by a keyboard 19 associated with a display screen 20 and controlled by a computer connected to the machine for cleaning and qualifying a dialysis filter.

Figure 3:
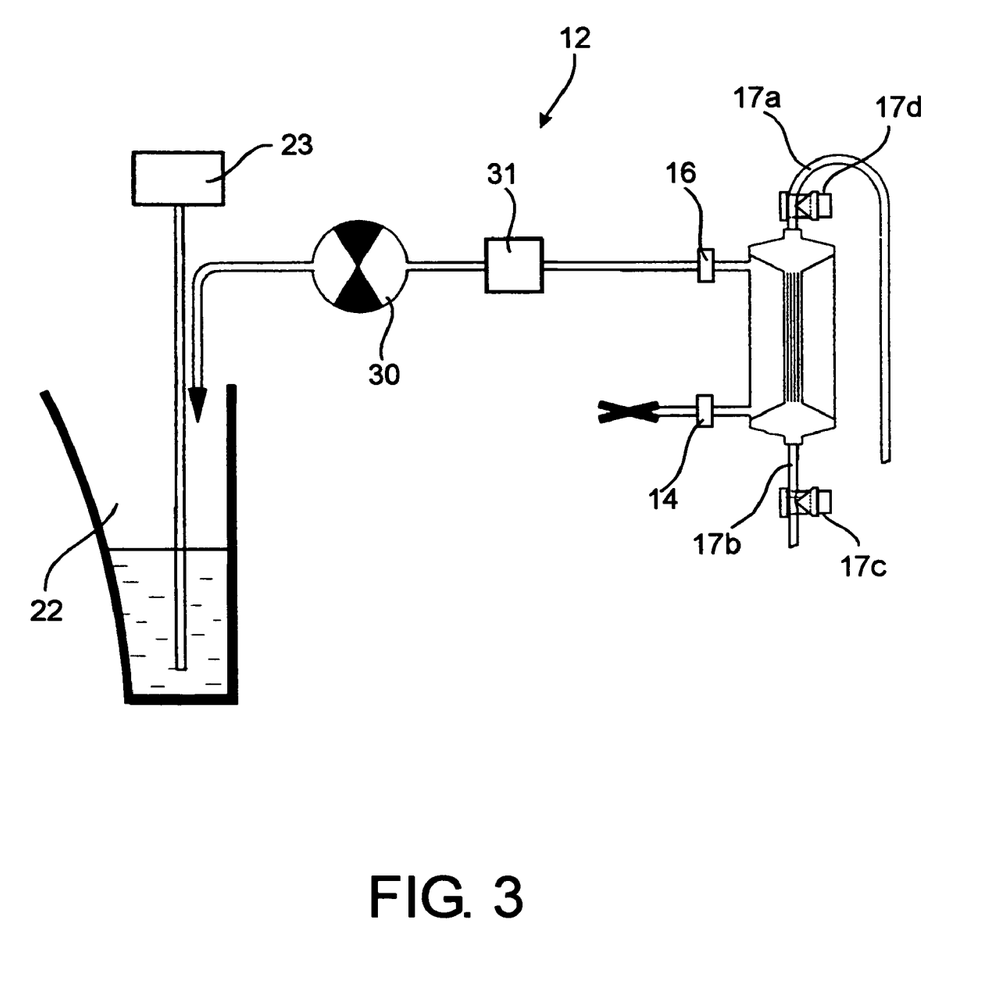
FIG. 3 is a schematic representation of the control device for filter performance in preparation for qualification.

The device (12) for controlling the performance of dialysis filter 100 (see FIG. 3), that is, its rate of ultrafiltration, is based upon the continuous measurement of liquid volume contained in the blood compartment of the filter by suctioning this liquid through the membrane. Given that the liquid passes through the membrane but no air passes through, if the filter is not damaged, the volume of water suctioned is essentially equal to the volume in the blood compartment. Measuring the volume of liquid passing through the membrane as a function of time produces a curve representative of the condition of the membrane.

Figure 4:
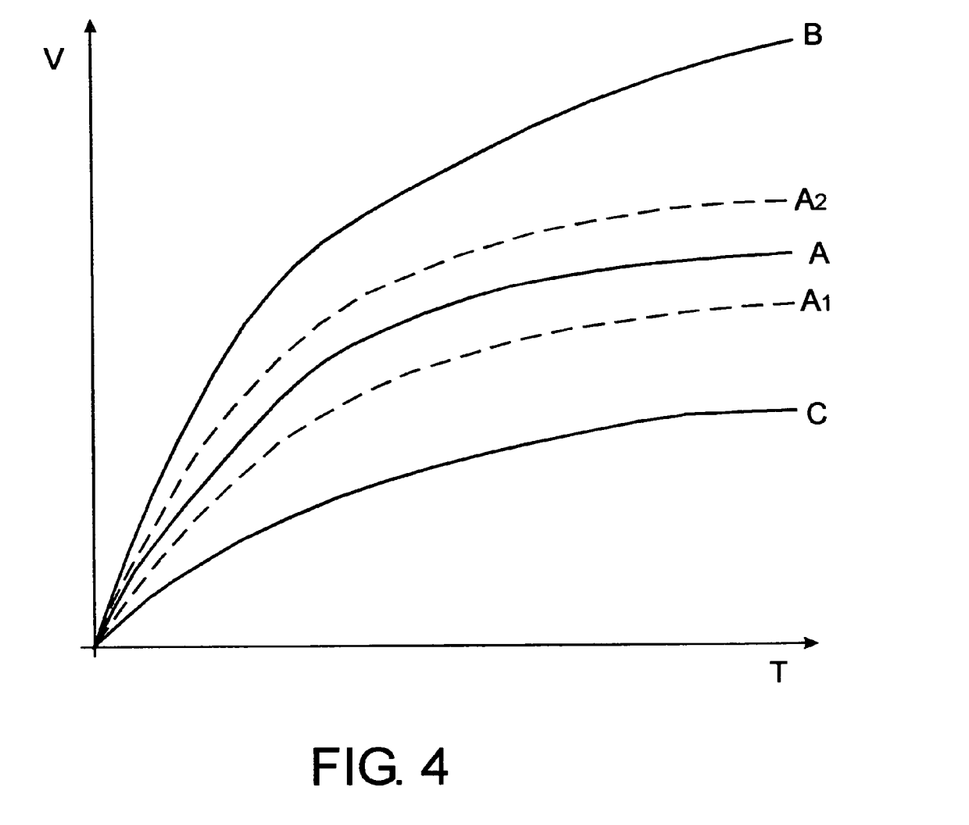
FIG. 4 is a schematic representation of the curves depicting ultrafiltration performance by the membrane or filter in various states.

FIG. 4 shows the curves that are characteristic of dialysis filters with their membranes in perfect condition, filters with defective membranes, specifically perforated or torn membranes, and filters with partially blocked membranes.

In order to perform this measurement, control device 12 (see FIG. 2) comprises a depressurization generator, for example a pump 30, connected through connecting tip 16 to dialysate compartment 100a of the filter. The filter is filled, that is, the first dialysate compartment 100a and the second compartment 100b, with liquid, for example, water. Valve 14 and throttle valves 17c and 17d are closed. Valve 16 is open to allow connecting tip 15 to be connected to a water loss compensation device (not shown) and a pressure regulator 31. Pump 30 begins to generate suction when at least throttle valve 17d is opened. If membrane 110 is in perfect condition, the water in said second blood compartment 100b passes through this membrane and fills the first dialysate compartment 100a. Second blood compartment 100b empties progressively and a volume of water equivalent to the volume of this compartment is collected in a receptacle called the measurement container 22. This receptacle has a specific shape, i.e., its walls are adapted to define an essentially logarithmic measurement scale in order to maintain the same degree of precision regardless of the volume of liquid collected. At the beginning of the operation a small amount is collected and the variation in height measured by probe 23 is relatively large, whereas at the end of the operation, the volume measured is larger and the variation in height is smaller. The measurement curve corresponding to a new filter in good condition is curve A in FIG. 4. This curve must be located within a range of tolerance defined by the two curves A1 and A2 shown by dashed lines. The slope of curve A defines the microfiltration rate that allows the filter to be qualified.

When membrane 110 of filter 100 is torn in certain locations, it allows air to pass through, at least partially filling first dialysate compartment 100a. The water in this first compartment is suctioned by pump 30 so the measurement receptacle is filled more quickly. The corresponding curve is curve B on the graph in FIG. 4. The slope of the curve is larger and if it is greater than the slope of curve A2, as shown in FIG. 4, the filter is considered to be defective.

When membrane 110 of filter 100 is blocked in certain locations, it slows the passage of the water in second blood compartment 100b toward first dialysate compartment 100a, which is connected to pump 30. The water in this first compartment is suctioned more slowly by pump 30, and as a result, the measurement container is filled more slowly. The corresponding curve is curve C on the graph in FIG. 4. The slope of the curve is less steep and if it is smaller than the slope of curve A1, as shown in FIG. 4, the filter is considered to be defective.

During measurement, the lowered pressure generated by pump 30 is maintained constant through the use of a pressure regulator 31. Container 22 is associated with a probe 23 which measures variations in the height of the liquid in the container and sends the measurement results to a processor, where they are recorded and stored in a computer in order to monitor the evolution of filter characteristics over time.

These measurements offer the further advantage of defining the type of defect present in the filter, since:

if the total amount of liquid suctioned is less than the amount obtained with a new filter, it may be deduced that the membrane fibers are blocked;

if the liquid continues to migrate once the blood compartment is emptied, it may be deduced that the fibers are broken and that the membrane is torn;

if the total amount suctioned remains constant but is suctioned over a longer period of time, it may be deduced that the pores in the membrane are blocked; and conversely, if this same total amount of liquid is suctioned over a shorter period of time, it may be deduced that the pores in the membrane are dilated.

To guarantee complete safety, dialysis cleaning machine 10 is further provided with a means of identifying the filter, and consequently the patient to whom the filter is attributed, as well as the person operating the machine. These identification means consist of transponder cards similar to a touch-free credit card which stores various parameters. These cards are associated with a reader 40 incorporated in machine 10. The parameters recorded are first, those relating to the filter:

the identity of the patient and data specific to the treatment of his or her filter;
the type of filter;
the number of regenerations authorized
the measurement tolerances;
the results of last control performed;
the identity of the last operator who treated the filter;
and also relating to the operator:
identity (name and number); and
level of privilege.

The consideration of all these parameters that have been automatically processed by the computer and the use of transponders significantly reduces the risk of mishandling or error. Moreover, a filter which, upon measurement, does not conform to the criteria established by the patient's doctor is automatically rejected because the machine becomes blocked.

The present invention is not limited to the preferred embodiment described, but it may undergo different modifications or variations obvious to a person skilled in the art. In particular, the machine may include more or fewer than three processing stations within the same unit that are completely independent of each other.

The invention claimed is

1. A machine for cleaning and qualifying a dialysis filter comprising a first dialysate compartment having a first connecting tip and a second connecting tip, and a second blood compartment comprising two conduits that are joined at first and second extremities of the second blood compartment, the first dialysate compartment and the second blood compartment being separated by an ultrafiltration membrane that is liquid-permeable but not air-permeable located inside the filter, wherein the machine comprises a first rinse circuit comprising the first dialysate compartment (100a), the first connecting tip (13) connected to a lower portion of the first dialysate compartment (100a) and the second connecting tip (15) connected to an upper portion of the first dialysate compartment (100a); a second rinse circuit comprising the second blood compartment (100b) and the two conduits (17a and 17b) joined at the first and second extremities of the second blood compartment (100b), the second rinse circuit is totally independent of the first rinse circuit; a first means for supplying exclusively the first rinse circuit with a cleaning and disinfecting liquid injected through the first tip (13) connected to the lower portion of the first dialysate compartment (100a); a second means for exclusively supplying the second rinse circuit with the cleaning and disinfecting liquid from the first rinse circuit, said second means being an ultrafiltration membrane (110) that is liquid-permeable but not air-permeable and said cleaning and disinfecting liquid flowing through said ultrafiltration membrane by untrafiltration; and a qualifying means to determine the ultrafiltration rate of the ultrafiltration membrane (110) that is liquid-permeable but not air-permeable comprising means of generating lowered pressure in said first dialysate compartment (100a) by the second connecting tip (15) connected to the upper portion of the first dialysate compartment (100a) so as to suction at least a quantity of liquid essentially equivalent to the liquid contained in the second blood compartment (100b) by ultrafiltration through the ultrafiltration membrane (110) that is liquid-permeable but not air-permeable, and means for determining a slope of a curve of the quantity of liquid suctioned as a function of time, and the two conduits (17a and 17b), joined at the first and the second extremities of the second compartment (100b), are respectively associated with two throttle valves (17d and 17c) and respectively flow into recovery containers (18a, 18b, respectively) for direct removal of contaminated cleaning and disinfecting liquid from the second blood compartment (100b).

2. The machine according to claim 1, wherein the machine further comprises a pump (30) connected to the second connecting tip (15) joined to the upper portion of said first dialysate compartment (100a).

3. The machine according to claim 1, wherein the machine further comprises a pressure regulator (31) also connected to the second connecting tip (15) joined to the upper portion of the first dialysate compartment (100a).

4. The machine according to claim 1, wherein the machine comprises a measurement container (22) which is connected, via a pump (30), to the second connecting tip (15), such that the liquid pumped from the first dialysate compartment (100a) is collected, and a measurement probe (23) for measuring variations in a level of the liquid collected in the measurement container (22).

5. The machine according to claim 4, wherein walls of the measurement container (22) are adapted to define an essentially logarithmic measurement scale in order to maintain a same degree of precision regardless of a volume of liquid collected in the container.

6. The machine according to claim 1, wherein a means of qualifying the filter (100) comprises an automatic means of identifying the filter and a machine operator.

7. The machine according to claim 6, wherein the means of identifying the filter comprises a transponder card respectively attributed to the filter and to the operator.

8. The machine according to claim 6, wherein the means of qualifying the filter (100) comprises a card reader (40) respectively attributed to the filter and to the operator.

9. The machine according to claim 1, wherein the means of qualifying the filter (100) comprises a means of automatically recording data regarding the qualified filter, parameters of a patient to whom the filter is attributed, and results of the measurements performed.

10. The machine according to claim 1, wherein the ultrafiltration membrane (110) has a porosity which prevents the passage of virus and bacteria therethrough.

11. A machine for simultaneously cleaning and qualifying a plurality of dialysis filters, each filter having a dialysate compartment and a blood compartment, the dialysate compartment and the blood compartment being separated by an ultrafiltration membrane that is liquid-permeable but not air-permeable, the machine comprising a plurality of cleaning and qualifying stations, each cleaning and qualifying station comprising;

a means of identifying the particular filter (100) and recalling previously recorded data related to the particular filter (100);

a first rinse circuit comprising the dialysate compartment (100*a*) of the filter (100), a first connecting tip (13) connected to a lower portion of the dialysate compartment (100*a*) and a second connecting tip (15) connected to an upper portion of the dialysate compartment (100*a*);

a second rinse circuit, which is totally independent of the first rinse circuit, comprising the blood compartment (100*b*) of the filter (100), a first conduit (17*a*) coupled to the blood compartment (100*b*) at a first extremity thereof and extending from the blood compartment (100*b*) to a first recovery container (18*a*) and a second conduit (17*b*) coupled to the blood compartment (100*b*) at an opposed second extremity thereof and extending from the blood compartment (100*b*) to a second recovery container (18*b*), each of the first conduit (17*a*) and the second conduit (17*b*) having a throttle valve (17*d*, 17*c*) located between the blood compartment (100*b*) and a respective one of the first recovery container (18*a*) and the second recovery container (18*b*);

a first supply means coupled to the first connecting tip (13) for exclusively supplying the first rinse circuit with a cleaning and disinfecting liquid;

a second supply means for exclusively supplying the second rinse circuit with the cleaning and disinfecting liquid from the first rinse circuit, the second supply means being the ultrafiltration membrane (110);

a qualifying means to determine an ultrafiltration rate of the cleaning and disinfecting liquid through the ultrafiltration membrane (110), the qualifying means comprising,         a means of reducing pressure in the dialysate compartment (100*a*) coupled to the second connecting tip (15) to draw a quantity of liquid from the dialysate compartment (100*a*), the quantity of liquid being essentially equivalent to a quantity of liquid in the blood compartment (100*b*) simultaneously being drawn through the ultrafiltration membrane (110) into the dialysate compartment (100*a*);

a means of quantifying the quantity of liquid drawn from the dialysate compartment (100*a*) as a function of time; and     a means of recording data from the qualifying means and associating the data with the particular filter (100).

* * * * *